United States Patent [19]

Milana et al.

[11] 4,296,333

[45] Oct. 20, 1981

[54] METHOD AND APPARATUS FOR DETECTING SURFACE DEFECTS IN A WORKPIECE

[75] Inventors: Emilio Milana, Rivalta; Franco Rasello, Gabiano, both of Italy

[73] Assignee: Centro Ricerche Fiat S.p.A., Orbassano, Italy

[21] Appl. No.: 74,027

[22] Filed: Sep. 10, 1979

[30] Foreign Application Priority Data

Oct. 24, 1978 [IT] Italy .................. 69439 A/78

[51] Int. Cl.$^3$ .................................. G01N 21/48
[52] U.S. Cl. .................... 250/572; 356/446
[58] Field of Search ............. 356/446, 447, 448, 445; 250/572, 562, 563

[56] References Cited

U.S. PATENT DOCUMENTS 4,097,160  6/1978  Yataki et al. .............. 356/446 X
4,162,126  7/1979  Nakagawa et al. ......... 356/446 X

*Primary Examiner*—David C. Nelms
*Assistant Examiner*—Darwin R. Hostetter
*Attorney, Agent, or Firm*—Sughrue, Mion, Zinn, Macpeak and Seas

[57] ABSTRACT

Quality control inspection of the surface of a workpiece is effected by scanning a coherent monochromatic light beam over the workpiece surface. Photomultipliers are used to generate two electrical signals respectively indicative of the magnitude of the specular component of light reflected from the workpiece and of the component of light scattered in a predetermined direction off the workpiece. These two signals are combined in a manner which serves to eliminate noise due to surface roughness of the workpiece. The combined signal is compared with a threshold value to provide an indication of surface defects. The inspection apparatus can incorporate a laser for producing the light beam which can be conveniently scanned across the workpiece surface using an oscillating mirror.

7 Claims, 2 Drawing Figures

METHOD AND APPARATUS FOR DETECTING SURFACE DEFECTS IN A WORKPIECE

This invention relates to a method and apparatus for detecting surface defects in a workpiece which has undergone a mechanical operation.

The object of the present invention is to facilitate quality control inspection of workpieces directly after they have been subjected to a mechanical operation in order to provide an immediate warning of any surface defects present in the workpiece such as for example perforations, scoring and dents.

According to one aspect of the present invention, there is provided a method of detecting surface defects in a workpiece which has undergone a mechanical operation, characterized in that the method comprises the steps of:

directing coherent monochromatic light radiation on to the surface of the workpiece in a direction normal thereto;

moving the light radiation and workpiece relative to each other whereby to effectively scan an area of the workpiece surface with the light radiation;

directing the specular component of the radiation reflected by each point of the scanned area of said surface to a first photomultiplier arranged to output an electrical signal indicative of the intensity of said specular component;

directing the component of radiation scattered along a predetermined direction from each point of the scanned area of said surface to a second photomultiplier arranged to output an electrical signal indicative of the intensity of said scattered component;

processing the output signals from the first and second photomultipliers so as to obtain a resultant signal substantially depurated of signal noise due to the surface roughness of the workpiece;

comparing said resultant signal with a reference threshold whereby to derive an indication of the presence of possible surface defects in the workpiece.

According to another aspect of the invention, there is provided apparatus for detecting surface defects in a workpiece which has undergone a mechanical operation, characterized in that the apparatus comprises a support for a workpiece to be examined; a source of coherent, monochromatic light radiation; a first optical system for directing light radiation emitted from said source on to the surface of a workpiece mounted on said support in a direction normal to said surface; an arrangement for moving said light radiation and support relative to each other whereby to scan the radiation over an area of said workpiece surface; a first photomultiplier; a second optical system for directing the specular component of the radiation reflected by each point of the scanned area of said workpiece surface to the first photomultiplier so as to obtain, at the output of said first photomultiplier a signal indicative of the intensity of said specular component; a second photomultiplier arranged to receive the component of radiation scattered along a predetermined direction from each point of the scanned area of said workpiece surface and to output a signal indicative of the intensity of said scattered component; and an electronic processing circuit connected to receive the output signals from said first and second photomultipliers, said processing circuit being arranged to derive from said output signals a resultant signal substantially depurated of signal noise caused by surface roughness of said workpiece, said processing circuit being further arranged to compare the said resultant signal with a reference threshold whereby to derive an indication of the presence of possible surface defects in the workpiece.

A method according to the invention and apparatus embodying the invention, both for detecting surface defects in workpieces, will now be particularly described by way of example, with reference to the accompanying diagrammatic drawings, in which.

Figure 1:
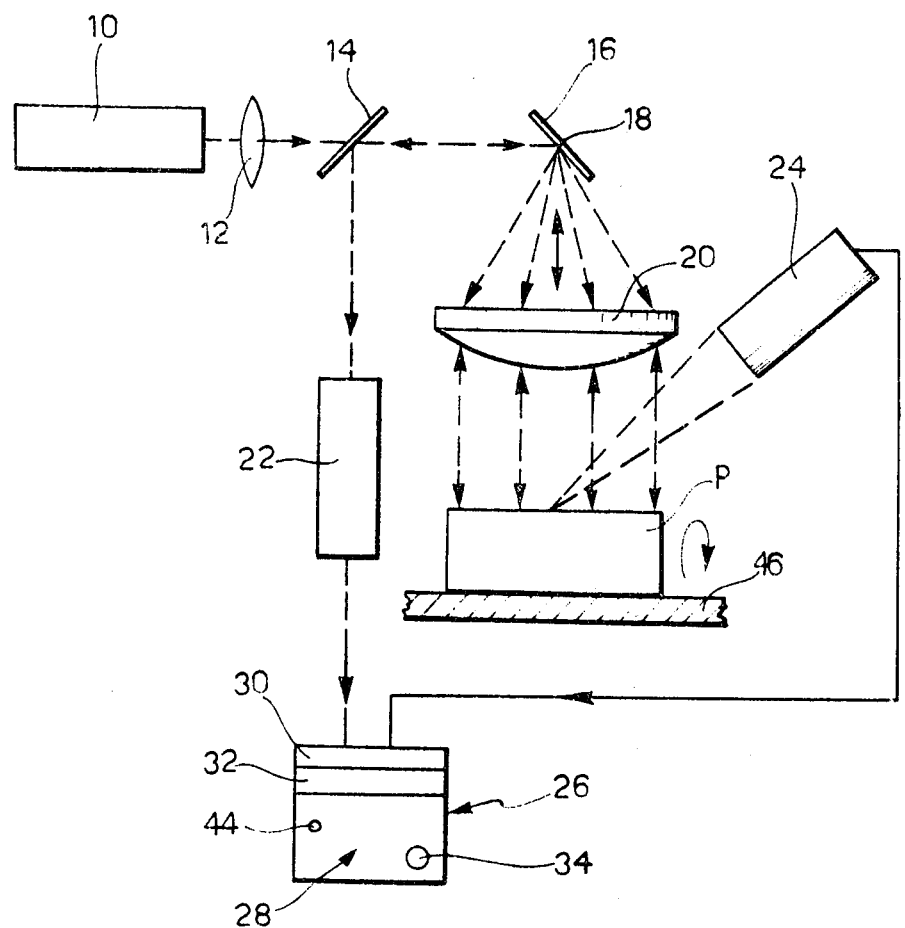
FIG. 1 is a schematic elevation of the surface-defect detection apparatus.

As shown in the drawings, the surface-defect detection apparatus comprises a source of coherent, monochromatic light which in the present example is a laser 10, and a focusing lens 12, positioned a short distance in front of the laser 10 and serving to focus into a beam the light emitted by the laser 10.

A semi-transparent mirror 14 and a mirror 16 are spaced from each other along the axis of the focusing lens 12. The mirror 16 is centrally pivoted about an horizontal axis 18 passing through the focus of a cylindrical lens 20 positioned beneath the mirror 16. The mirror 16 can be made to oscillate about the axis 18 with a frequency of around 50 Hz by a device (not shown), which for example is constituted by a galvanometer fed with an electrical signal of triangular form.

A first photomultiplier 22 is positioned below the semi-transparent mirror 14, and a second photomultiplier 24 is located adjacent the cylindrical lens 10 with its light inlet aperture facing downwards. The axis of the second photomultiplier 24 makes a predetermined angle with respect to the optical axis of the cylindrical lens 20, which in the example illustrated is approximately 50".

The outputs of the photomultipliers 22 and 24 are fed to a processing unit 26 having an external control panel 28 which mounts two monitors 30, 32 respectively arranged to display the levels of the signals coming from the photomultipliers, 22 and 24 and an indicator light 34.

Figure 2:
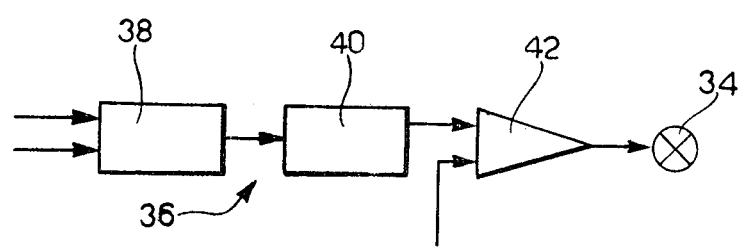
FIG. 2 is a block diagram of a signal processing unit of the apparatus.

The electronic circuitry 36 (FIG. 2) of the processing unit 26 includes a summing circuit 38 having two inputs connected with the outputs of the photomultipliers 22 and 24, and an output connected to the input of a squaring circuit 40.

The output of the squaring circuit 40 is connected to one input of a variable-threshold comparator 42 the other input of which is connected to a regulating potentiometer 44 mounted on the panel 28 of the processing unit 26.

The output of the comparator 42 is connected to the indicator light 34.

The laser 10, the lenses 12 and 20, the mirrors 14 and 16 and the photomultipliers 22 and 24 can be located and mounted inside a protective enclosure, not illustrated in the drawings, having a transparent portion arranged in correspondence to the cylindrical lens 20 and the inlet aperture of the second photomultiplier 24.

During use, the apparatus is positioned above a support 46 on which is mounted a workpiece P which has undergone a mechanical operation and is to be inspected; the mutual arrangement of the apparatus and the workpiece P is such that the optical axis of the cylindrical lens 20 is perpendicular to the surface of the workpiece P. In the example illustrated, the workpiece P is constituted by a piston for automobile brakes. Next, the laser 10 is energised to emit a beam of coherent, monochromatic light. Said beam of light passes through the focusing lens 12 and the semi-transparent mirror 14 to strike the mirror 16 at a point corresponding to the focus of the cylindrical lens 20. As a result, the light reflected through the lens 20 by the mirror 16 will strike the surface of the workpiece P at right angles. The lens 12 and 20 and the mirrors 14 and 16 thus form a first optical system operative to direct light radiation onto the surface of the workpiece (P) perpendicularly thereto.

By making the mirror 16 oscillate about the axis 18, the light beam from the laser 10 effects a back and forth scanning motion of predetermined amplitude across the surface of the cylindrical lens 20 and thus across the workpiece surface (the lens 20 maintaining the perpendicularity of the scanning light beam relative to the surface of the workpiece P). In the example illustrated, in which the workpiece P is constituted by a cylindrical piston, the scanned area of the workpiece is a strip extending along a generatrix of the piston.

In the present case, the scanning of the beam is effected by the arrangement comprising the mirror 16 and the associated device for oscillating this mirror; it is, however, possible to effect the desired scanning by any suitable arrangement for moving the light beam and workpiece P relative to each other.

Upon the scanning light beam striking the surface of the workpiece P, it is reflected with part of the beam undergoing scattering (irregular reflection). The specular component of the light radiation reflected by each point of the scanned area passes back through the cylindrical lens 20 and is directed by the mirror 16 and the semi-transparent mirror 14, to the inlet aperture of the first photomultiplier 22. The lens 20 and mirrors 14 and 16 thus serve as a second optical system directing the specular component of reflected radiation to the first photomultiplier 22. At the same time, a component of said scattered radiation is reflected towards the inlet aperture of the second photomultiplier 24, this component having an inclination with respect of the optical axis of the cylindrical lens 20 substantially equal to the inclination of the axis of the second photomultiplier 24. The output signals from the photomultipliers 22 and 24 are fed, via the monitors 30 and 32, to the processing circuitry 36 where they are added together by the summing circuit 38 in order to reduce signal noise caused by the surface roughness of the workpiece P. The output signal from the summing circuit 38 is fed to the squaring circuit 40 which proceeds to multiply said signal by itself to effectively amplify the peaks of the signal relative to the mean level of the signal itself.

The signal coming out from the squaring circuit 40 is fed to one input of the comparator 42, whose second input is fed with a predetermined threshold signal which can be automatically or manually varied by adjustment of the potentiometer 44.

When the scanning light beam scans across a surface defect in the workpiece P (for example a perforation, a scratch or a dent), the levels of the output signals from the photomultipliers 22, 24 exhibit a sudden variation, which will generally be negative since such surface defects can be considered as absorption centres of the incident light energy. If the signal level variation is such that the resultant output from the squaring circuit 40, crosses the predetermined threshold, the comparator 42 will output a signal operative to switch on the indicator light 34.

In the case of the example illustrated, in which the workpiece P under examination has a cylindrical profile, it is possible to examine the whole surface of the workpiece P by scanning the surface in strips parallel to its generatrixes with successive surface strips being brought under the scanning light beam by rotation of the workpiece P about its axis.

Since the effective absorption of incident light energy caused by the presence of a surface defect in the workpiece is more apparent the smaller the light beam emitted by the laser 10 is relative to the transverse dimension of the defect, it is possible to vary the sensitivity of the apparatus by interposing between the focusing lens 12 and the mirror 14 a second lens (not illustrated) with shorter focus than that of the lens 12, which serves to narrow the size of the beam.

From the preceding description it will be apparent that the described apparatus is reliable, accurate, and easy to use, and does not require complex setting up operations or calibration. The apparatus can be advantageously used directly at the end of a production line in order to carry out quality control examination of finished workpieces immediately after their manufacture.

It will of course be appreciated that various modifications are possible to the form and construction of the apparatus described above, for example, the electronic circuitry of the processing unit 26 can be built around a microprocessor.

We claim:

1. A method of detecting surface defects in a workpiece which has undergone a mechanical operation, the method comprising the steps of:

directing a beam of coherent monochromatic light radiation onto the surface of the workpiece in a direction normal thereto;

moving the light radiation beam and workpiece relative to each other whereby to effectively scan an area of the workpiece surface with the light radiation beam;

directing the specular component of the radiation beam which is reflected perpendicular to the workpiece by each point of the scanned area of said surface to a first photomultiplier arranged to output an electrical signal indicative of the intensity of said specular component;

sampling the component of radiation beam scattered from each point of the scanned area of said surface via a second photomultiplier arranged to output an electrical signal indicative of the intensity of said scattered component;

processing the output signals from the first and second photomultipliers so as to obtain a resultant signal substantially free of signal noise due to the surface roughness of the workpiece; and comparing said resultant signal with a reference threshold whereby to derive an indication of the presence of possible surface defects in the workpiece.

2. A method according to claim 1, wherein the step of processing the output signals from the first and second photomultipliers comprises positively summing together said output signals and multiplying the signal thus obtained by itself so as to amplify the peaks of the signal relative to the mean level of said signal.

3. Apparatus for detecting surface defects in a workpiece which has undergone a mechanical operation, said apparatus comprising
- a support for a workpiece to be examined;
- a source of coherent monochromatic light radiation;
- a first optical system for direction a beam of light radiation emitted from said source onto the surface of a workpiece mounted on said support in a direction normal to said surface;
- an arrangement for moving said light radiation beam and support relative to each other whereby to scan said radiation beam over an area of said workpiece surface;
- a first photomultiplier;
- a second optical system for directing the specular component of the radiation beam which is reflected perpendicular to the workpiece by each point of the scanned area of said workpiece surface to the first photomultiplier so as to obtain, at the output of said first photomultiplier, a signal indicative of the intensity of said specular component;
- a second photomultiplier arranged to receive the component of radiation scattered from each point of the scanned area of said workpiece surface and to output a signal indicative of the intensity of said scattered component; and
- an electronic processing circuit connected to receive the output signals from said first and second photomultipliers, said processing circuit being arranged to derive from said output signals a resultant signal substantially free of signal noise caused by surface roughness of said workpiece, said processing circuit being further arranged to compare the said resultant signal with a reference threshold whereby to derive an indication of the presence of possible surface defects in the workpiece.

4. Apparatus according to claim 3, wherein said light radiation source is a laser.

5. Apparatus according to claim 3 or claim 4, wherein the first optical system and the said arrangement for moving the light radiation and support relative to each other are combined such that the light radiation undergoes a scanning motion with the support stationary.

6. Apparatus according to claim 5, wherein said first and second optical systems together comprise
- a focusing lens,
- a semi-transparent mirror,
- a mirror for deflecting the radiation emitted by said light radiation source, said radiation arriving at said mirror through the focusing lens and the semi-transparent mirror,
- a cylindrical lens arranged with its focal line passing through the point of the mirror struck by the radiation from said source and having its optical axis perpendicular to the surface of the workpiece to be examined, and,
- a device for oscillating the mirror around an axis parallel to the surface of the workpiece and passing through the focus of the cylindrical lens, said semi-transparent mirror being arranged to deflect towards the first photomultiplier the specular component of the radiation reflected from each point of the scanned area of said workpiece surface, said specular component arriving at said first photomultiplier by transmission back through the cylindrical lens and subsequent reflection by the said mirror and said semi-transparent mirror.

7. Apparatus according to claim 3, wherein said electronic processing circuit comprises
- a summing circuit for summing together the output signals from the photomultipliers,
- a squaring circuit for multiplying the output signal from said summing circuit by itself, and
- a comparator for comparing the output signal from said squaring circuit with a predetermined threshold signal whereby to determine whether the level of the peaks of said output signal crosses the threshold level.

* * * * *